United States Patent [19]

Seprödi et al.

[11] Patent Number: 4,948,873

[45] Date of Patent: Aug. 14, 1990

[54] GONADOLIBERINE ANALOGUES OF HIGH ACTIVITY

[75] Inventors: János Seprödi; István Teplán; István Schón; Judit Erchegyi, all of Budapest; Zsolt Vadász, Tardosbánya; Olga N. née Kuprina, Budapest; Tamás Szirtes, Budapest; András Selmezci, Budapest; Béla Kanyicska, Kerepestarcsa, all of Hungary

[73] Assignee: Richter Gedeon Vegyeszeti Gyar, Budapest, Hungary

[21] Appl. No.: 921,770

[22] Filed: Oct. 21, 1986

[30] Foreign Application Priority Data

Oct. 22, 1985 [HU] Hungary ............... 4070/85

[51] Int. Cl.$^5$ ............................................. C07K 7/02
[52] U.S. Cl. ..................................... 530/328; 514/800; 530/313
[58] Field of Search ................. 530/328, 313; 514/15, 514/800, 16

[56] References Cited

U.S. PATENT DOCUMENTS

| | | |
|---|---|---|
| 3,749,705 | 7/1973 | Sakakibara et al. ............... 530/321 |
| 3,888,836 | 6/1975 | Veber et al. ...................... 530/313 |
| 4,382,922 | 5/1983 | Rivier et al. ...................... 514/15 |
| 4,410,514 | 10/1983 | Vale, Jr. et al. .................. 514/15 |
| 4,472,382 | 9/1984 | Labrie et al. ..................... 530/328 |
| 4,512,923 | 4/1985 | Flegel et al. ..................... 530/313 |
| 4,569,927 | 2/1986 | Rivier et al. ..................... 530/328 |
| 4,600,705 | 7/1986 | Seprödi et al. ................... 514/15 |
| 4,677,193 | 6/1987 | Rivier et al. ..................... 530/313 |

FOREIGN PATENT DOCUMENTS

| | | |
|---|---|---|
| 897455 | 6/1982 | Belgium . |
| 165546 | 5/1972 | Hungary . |
| 4819318 | 6/1973 | Japan .................... 530/328 |
| 2138427 | 10/1984 | United Kingdom .......... 530/328 |

OTHER PUBLICATIONS

Organic Chemistry, Morisson & Boyd, 3rd ed., 1974, p. 353.
Int. J. Peptide Protein Res. 12, pp. 277–283 (1978).
Endocrine Reviews, 7/1, pp. 44–66 (1986).
Science, vol. 210–7, Nov. 1980, pp. 657–658, Bioactive Confirmation of Luteinizing Hormone–Releasing Hormone: Evidence from a Conformationally Constrained Analog.
J. Sandow et al, Control of Ovulation, Butterworths, London (1978), pp. 49–70.

*Primary Examiner*—Margaret Moskowitz
*Assistant Examiner*—T. D. Wessendorf
*Attorney, Agent, or Firm*—Herbert Dubno; Jonathan Myers

[57] ABSTRACT

The present invention relates to novel gonadoliberine analogues of formula I

Glp-His-Trp-Ser-X-W-Leu-Arg-Pro-Y     (I)

wherein
X is Phe-, Tyr (3,5-$^3$H) or 3,5-dibromo-tyrosyl,
W is Asu or Asp OR, wherein R is alkyl having 1 to 6 carbon atoms or phenyl or phenyl (alkyl having 1 to 4 carbon atoms), which latter two groups may optionally be substituted by nitro or one or more halogen atoms, and
Y is glycinamide, aza-glycinamide or alkylamino having 1 to 4 carbon atoms, and acid-addition salts thereof, processes for preparing the same and pharmaceutical compositions comprising the same.

The novel compounds have an influence on the sexual processes.

3 Claims, 1 Drawing Sheet

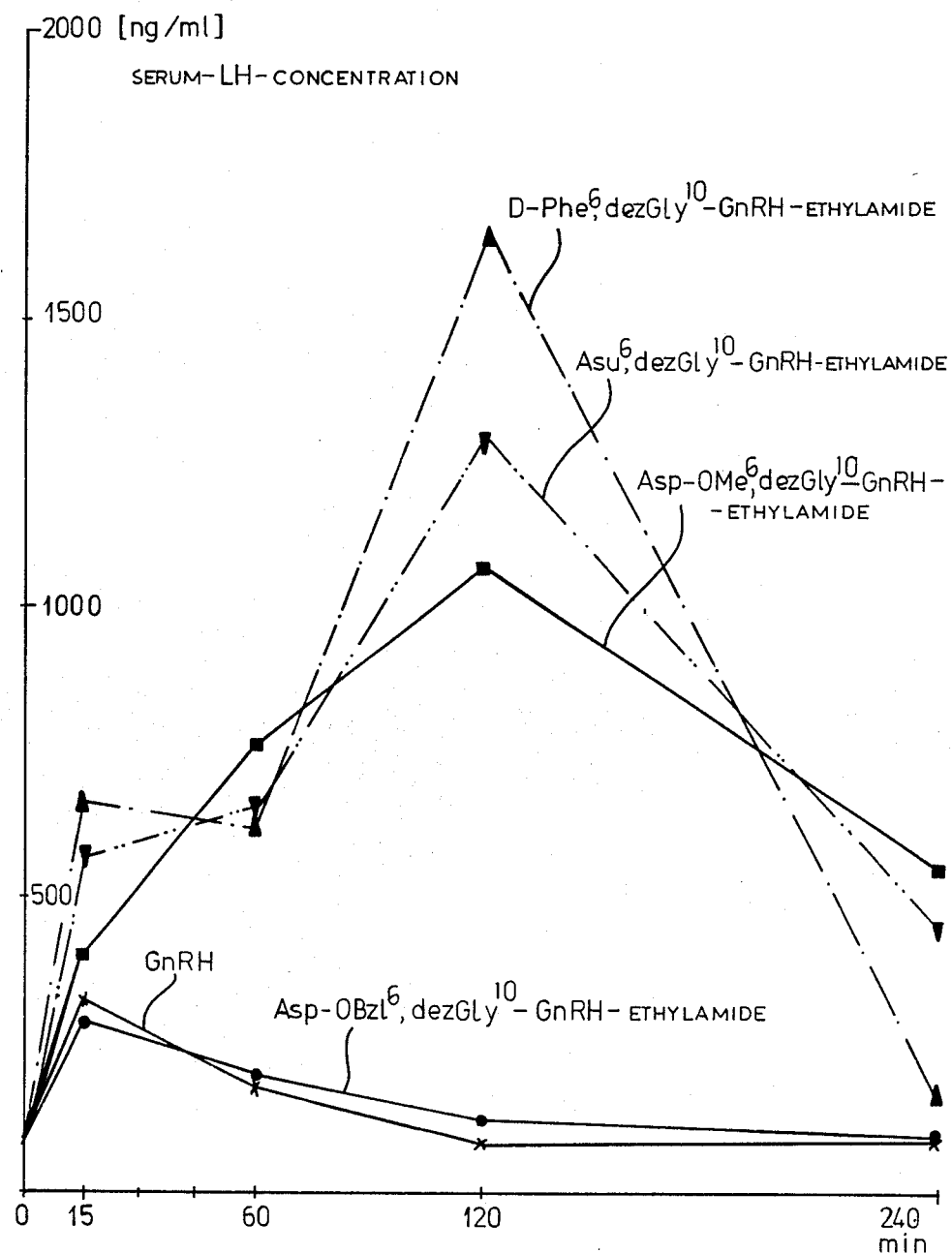

GONADOLIBERINE ANALOGUES OF HIGH ACTIVITY

TECHNICAL FIELD

The present invention relates to novel gonadoliberine analogue compounds (hereinafter GnRH analogues) of formula I Glp-His-Trp-Ser-X-W-Leu-Arg-Pro-Y (I)

and the acid-addition salts thereof, a process for preparing the same and use in therapy as therapeutic agents influencing the sexual processes.

In the above formula I

X is Phe—, Tyr(3,5-$^3$H) or 3,5-dibromo-tyrosyl,

W is Asu or Asp(OR), wherein R is alkyl having 1 to 6 carbon atoms or phenyl or phenyl (alkyl having 1 to 4 carbon atoms), which latter two groups may optionally be substituted by nitro or by one or more halogen atoms, and Y is glycinamide, aza-glycinamide or alkylamino having 1 to 4 carbon atoms.

The α-amino acids referred to in the specification are all of "L" configuration if it is not otherwise mentioned.

BACKGROUND ART

The native gonadoliberine peptide hormone of hypothalamic origin liberates the luteinising hormone (hereinafter LH) controlling the sexual processes and follicus stimulating hormone (hereinafter FSH). Through these hormones the rutting, ovulation, spermatogenesis, etc. which processes basically determine the natural proliferation of vertebrates may be stimulated or inhibited. On the bases of recent research the use of GnRH analogues in the therapy of prostata and malignant tumors seems to be promising.

Hungarian Patent Specification No. 165,546 describes the synthetic preparation of native GnRH. According to this known process the GnRH is prepared by condensing 6+4 fragments. In U.S. Pat. No. 3,888,836 the compound is built up step by step.

Knowing the therapeutical utility of GnRH, a high number of analogues were prepared of which the so-called superactive GnRH analogues are of especial importance. It is known (J. Sandow et al, Control of Ovulation, Butterworths, London, 1978: v. 49–70.) that if the Gly group being in position 6 of the native GnRH is replaced by any α-amino acid of D-configuration, the LH liberating effect of the GnRH analogue as well as the duration of the effect are highly increased.

In Belgian Patent Specification No. 897,455 such GnRH analogues are described, wherein the Gly group being in position 6 is replaced by a D-1-amino-3,3-dimethyl-1-butanoic acid.

U.S. Pat. No. 4,410,514 relates to superactive GnRH analgues wherein the 6-Gly is replaced by D-Trp, -Ala, Phe, -Lys, -Pro, -Met, -Leu, Glu, -Asn, -Arg, -Tyr, -Cys, -His, -Chg, -Nva, -Orn, Thr, -Abu, -Phg, -Ile,-Gln,-Asp,-Nle or -Val and the C-terminal Gly group is optionally missing and/or substituted. The target compounds are suggested to be used for the therapy of fishes.

U.S. Pat. No. 4,382,922 describes the 6-D-Phe GnRH analogues, while German Published Patent Application No. 24 38 350 relates to GnRH analogues having substituted D-Ser, Cys, Asp, Glu, Orn, and Lys groups in position 6. In Swiss Patent Specification No. 603,559 the amino acid groups being in positions 5, 6 and 7 are replaced by other amino acid groups mainly of D configuration. The prior art refers to numerous other publications relating to superactive GnRH analogues. The common feature of these analogues is that the amino acid group being in position 6 is derived from a non-native amino acid.

Those analogues wherein a β-amino acid is in position 6 have also a high GnRH activity (Hungarian patent specification No. 187,503).

The GnRH analogue wherein an L-gamma-lactame ring is in positions 6 and 7 also exhibits significant biological activity. [Science, 210, 656 (1980)]

It can be stated that all of the known analogues of GnRH comprise at least one structural element which cannot be found in nature. However, it is very favorable from the therapeutical point of view of peptide hormones of endogenic activity if the compound comprises exclusively native amino acids and it can be substantiated that the metabolic products of the active ingredient will not cause undesired side-effects.

The aim of our work was to develop GnRH analogues having more long lasting and higher LH liberating activity than the natural GnRH which are built up exclusively from L-α-amino acids.

Surprisingly we found that the compounds of formula I comprising no D-amino acid have much higher efficacity for liberating the LH hormone than the natural GnRH.

DETAILED DESCRIPTION OF THE INVENTION

According to the invention the GnRH analogues of formula I are prepared by a) reacting an optionally protected peptide of formula II V-W-Leu-Arg-Pro-Y (II)

wherein W and Y are the same as defined hereinabove, V is a t-butoxycarbonyl, benzyloxy carbonyl or 9-fluorenyl-methoxy-carbonyl protective group, with a pentapeptide azide formed in situ from a pentapeptide hydrazide of formula V Glp-His-Trp-Ser-X-NH-NH$_2$ (V)

after the removal of the protective group, or b) for the preparation of the GnRH analogues of formula I wherein W stands for an Asu-group, X, Y and R are the same as defined hereinabove, treating an optionally protected peptide of formula III Glp-His-Trp-Ser-X-Asp(OR)-Leu-Arg-Pro-Y (III)

wherein X, Y and R are the same as defined hereinabove, with an organic tertiary nitrogen base in an anhydrous organic solvent, or c) for the preparation of the GnRH analogues of formula I wherein W is Asu, and X, Y and R are the same as defined hereinabove, treating an optionally protected peptide of formula IV

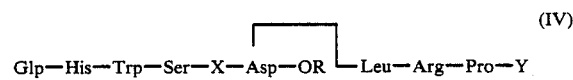

(IV)

wherein X, Y and R are the same as defined hereinabove with an organic tertiary nitrogen base in an anhydrous organic solvent, and if desired transforming the GnRH analogues of formula I thus obtained, wherein X, W and Y are the same as defined hereinabove, into pharmaceutically acceptable acid addition salts in a manner known per se.

In the process according to the invention preferably triethyl amine, N-methyl-morpholine or pyridine can be used as organic tertiary nitrogen base.

As organic solvent any polar, aprotic solvent may be used. It is preferred if dimethyl formamide is used as organic solvent with triethyl amine as organic base.

The optionally protected peptides used as starting materials in the process according to the invention can practically be prepared by fragment condensation or by increasing the length of the peptide chain step by step in a manner known per se in the peptide chemistry. E.g. certain elements of the peptide chain can be attached by the aid of an amino acid derivative activated in a manner known per se. Thus the peptides of formula I used in process variant a) as starting materials can be prepared by condensing an optionally protected peptide derivative of formula VI

H-Leu-Arg(Q)-Pro-Y     (VI)

wherein Y is the same as defined hereinabove, Q is nitro group or hydrogen atom, and an optionally protected amino acid derivative of formula VII

V-Asp(OR)-OH     (VII)

wherein R and V are the same as defined hereinabove, while the reactivity of the α-carboxyl group of the amino acid derivative of formula VII is enhanced by forming a reactive ester derivative and the activated derivative thus obtained is reacted with the peptide of formula VI and the nitro group being optionally present is removed.

In the course of process variants b) and c) the Asu-group is similarly formed, while the —OR group of the —Asp(OR)—or

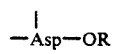

group is removed. The same reaction conditions are preferred to be maintained in both processes.

The peptides of formula I can be transformed into acid addition salts by reacting them with pharmaceutically acceptable acids. The compounds of formula I obtained in the form of a salt may be liberated by treating the salt with a base.

As an example for the alkyl groups having 1 to 6 carbon atoms standing for substituent R, the methyl, ethyl, n- and i-prop;1, n-, i-, sec- and tert-butyl and the straight and branched pentyl and hexyl groups may be mentioned. The preferred ones are the alkyl groups having 1 to 4 carbon atoms, especially preferred are the methyl and ethyl.

The substituents of the phenyl group in the optionally substituted phenyl and phenyl(C$_{1-4}$ alkyl) groups can take any position of the phenyl ring. As an example the 2-, 3- and 4-nitrophenyl, 2-, 3- and 4-chloro-, -bromo and fluorophenyl groups, the 2.4-. 3,5-dichloro-, -dibromo and difluoro-phenyl, the 2,4,6-trichloro-, -tribromo- and -trifluorophenyl groups, the di- and polyhalogen and/or -mono and polynitrophenyl groups wherein the halogen atoms and nitro groups are in optional combination can be mentioned which may also be substituted by the above-mentioned alkyl groups having 1 to 4 carbon atoms.

The GnRH analogues of formula I according to the invention can be transformed into pharmaceutical compositions in a manner known per se. The pharmaceutical compositions are preferably of solid or liquid form. As an example for the possible formulations the tablets, dragees, capsules, powder compositions and injection, inhalating, infusion formulations, the syrups and poultice liquids can be mentioned.

The present invention covers all of these formulations, the processes for preparing the same and the therapeutic methods when the ill human being or animal is treated with an effective dose of the GnRH analogues of formula I according to the invention.

The common feature of the superactive GnRH analogues is that they liberate many times the amount of LH hormone than the natural GnRH could do and the duration of their effect is also much longer. In order to illustrate the above statements the activity for liberating LH hormone of the natural GnRH analogues and some superactive and some representatives of the GnRH analogues of formula I according to the invention are shown in FIG. 1. The experiments were carried out on male mice, the active ingredient was administered subcutaneously and the LH content of the serum of the blood of the animals was measured by radioimmunoassay.

The figure clearly shows that the type and duration of the effect of the superactive GnRH analogues sharply alter from that of natural GnRH. It can also be seen that the effect of the GnRH analogues of formula I according to the invention is similar to that of the superactive GnRH analogues.

The difference may be explained by the supposition that upon addition of the superactive derivatives, the relative concentration of the biologically active structural isomers increases and their metabolic stability is higher than that of the natural substance.

Table I summarizes the biological data of a preferable representative of the GnRH analogues of formula I, Asu[6]-desGly[10]-GnRH-ethylamide.

TABLE I

The LH concentration in the serum in male mice
Dose: 200 ng/mouse

| Compound | LH serum level in mice after the treatments [ng/ml] | | |
|---|---|---|---|
| | 2 hours | 4 hours | 6 hours |
| GnRh | 85.2 | 81.4 | 87.0 |
| D-Phe[6],desGly[10]-GnRH-ethylamide | 648.1 | 131.5 | 67.8 |
| D-Ser tert-butyl[6], desGly[10]-GnRH-ethylamide | 1021.3 | 81.2 | 90.0 |
| Asu[6],desGly[10]-GnRH-ethylamide | 958.4 | 702.3 | 216.2 |

The toxicity data of Asu[6], desGly[10]-GnRH-ethylamide are as follows:

(a) When rats were administered a single dose of 10 mg/kg, the compound did not prove to be toxic.

(b) When rats were administered for 17 days a dose of 10 μg/rat, the compound proved to be atoxic.

(c) Inhibition of ovulation in rats

The compound was administered for 17 days in a dose of 0.5 μg/rats to sexually mature female rats. The inhibition of ovulation was 100%. The experimental method is described in B.B.R.C. 118, 351 (1958) Kovács et al.

(d) Induction of ovulation in angora rabbit

The sexually matured female rabbits were administered with a single does of 1.5 μg/rabbit, thereafter artificially inseminated. 90% of the animals became pregnant.

The invention is illustrated by the following, non-limiting examples. The thin-layer chromatographic $R_f$ values were determined on Kieselgel DC, Alufolien chromatoplates of Merck.

The following eluting mixtures were used (the ratios mean volume ratios):

| | | |
|---|---|---|
| 1. ethyl acetate/pyridine/acetic acid/water | 60:20:6:11 |
| 2. ethyl acetate/pyridine/acetic acid/water | 120:20:6:11 |
| 3. acetic acid/benzene | 1:7 |
| 4. n-butanol/acetic acid/water | 4:1:1 |
| 5. ethyl acetate/pyridine/acetic acid/water | 480:20:6:11 |
| 6. ethyl acetate/pyridine/acetic acid/water | 30:20:6:11 |
| 7. acetic acid/benzene | 1:15 |
| 8. acetone/toluene | 1:1 |
| 9. ethyl acetate/pyridine/acetic acid/water | 240:20:6:11 |
| 10. butanol/acetic acid/water/ethyl acetate | 1:1:1:1 |
| 11. the upper layer of butanol/acetic acid/water | 4:1:5 |
| 12. butanol/pyridine/acetic acid/water | 120:20:6:11 |
| 13. i-propanol/1 M aqueous acetic acid solution | 2:1 |
| 14. butanol/pyridine/acetic acid water | 45:20:6:11 |

The abbreviations of the amino acid and other groups are the same as it is commonly used in peptide chemistry. [J. Biol. Chem. 247, 977 (1972)]. The "Glp" is a pyroglutamyl group, while Dbt is a 3,5-dibromotyrosyl group.

EXAMPLE 1

Glp-His-Trp-Ser-Tyr-Asp(OMe)-Leu-Arg-Pro-ethylamide-bis(trifluoroacetate)

(a) Z-Asp(OMe)-Leu-Arg(NO₂)-Pro-ethylamide 3.77 g (8.4 millimoles) of Z-Asp(OMe)-OPFP in 60 ml of dimethyl formamide are cooled to a temperature 0° C., thereafter 3.76 g (7.0 millimoles) of H-Leu-Arg(NO₂)-Pro-ethylamide hydrogenbromide are added under stirring. Two hours later 1.16 ml (9.1 millimoles) of triethyl amine are added slowly, dropwise to the solution, and the stirring is maintained for another night at 0° C. Then the precipitated salt is filtered off, the filtrate is evaporated and the residual oil is dissolved in a mixture of 240 ml of ethyl acetate and 80 ml of 1M aqueous potassium hydrogensulphate. The organic phase is separated and extracted twice with 70 ml of 1M aqueous potassium hydrogensulfate and three times with 70 ml of saturated aqueous sodium chloride solution. Then it is dried over anhydrous magnesium sulfate, filtered and evaporated to dryness. The oily substance thus obtained is dissolved in 55 ml of hot ethyl acetate, the solution is cooled to a temperature of 30° C. and 400 ml of ether are slowly added dropwise. Ether is decanted from the precipitated substance, and the residue is triturated with ether. 3.60 g (72%) of the title compound are obtained after drying.

Molar weight: 719.

Melting point: 95°–105° C. $[\alpha]_D^{25} = -66.8°$ (c=1, methanol)

$R_f^2 = 0.68$; $R_f^9 = 0.23$; $R_f^{12} = 0.67$.

(b) H-Asp(OMe)-Leu-Arg-Pro-ethylamide diacetate 2.16 g (3.0 millimoles) of Z-Asp(OMe)-Leu-Arg(NO₂)-Pro-ethylamide are dissolved in a mixture of 24 ml of methanol and 24 ml of acetic acid, thereafter 900 mg of 10% palladium-on-charcoal catalyst suspended in 24 ml of water are added under stirring and hydrogen gas is bubbled through the reaction mixture for 8 hours. Then the catalyst is filtered off, the filtrate is evaporated and the residue is triturated with ether and dried. Thus 1.73 g (87.3%) of title product are obtained.

Molar weight: 660.

$[\alpha]_D^{25} = 57.0°$ (c=0.5, methanol)

$R_f^6 = 0.54$; $R_f^1 = 0.10$;

$R_f^4 = 0.22$; $R_f^{13} = 0.46$.

(c) Glp-His-Trp-Ser-Tyr-Asp(OMe)-Leu-Arg-Pro-ethylamide-bis(trifluoroacetate)

651 mg (0.908 millimoles) of Glp-His-Trp-Ser-Tyr-N₂H₃ pentapeptide hydrazide are dissolved in 6 ml of dimethyl formamide, the solution is cooled to a temperature of −15° C. and 0.61 ml of 6N hydrogen chloride/dioxane solution (3.63 millimoles) are added under stirring. Maintaining the temperature of the reaction mixture at −15° C., 62.6 mg (0.907 millimoles) of sodium nitrite are added in the form of a concentrated aqueous solution under stirring, then the reaction mixture is stirred for further 15 minutes at a temperature of −15° to −20° C. Then 545 mg (0.826 millimoles) of H-AspOMe-Leu-Arg-Pro-ethylamide diacetate salt in 6 ml of dimethyl formamide, cooled to a temperature of −15° C. are added to the above azide solution then just after 0.50 ml (3.632 millimoles) of triethyl amine are added. Thus the pH of the reaction mixture turns about 8. Thereafter the reaction mixture is stirred at a temperature of −10° C. to −15° C. for 30 minutes, then at 0° C. Three hours later the pH of the reaction mixture is adjusted to about 7 by the addition of 60 μl of 6N dioxanic hydrogen chloride solution (0.36 millimols), and the stirring is continued for another 60 hours at the same temperature. Then the precipitate is filtered off, the filtrate is evaporated and the oily substance obtained as an evaporation residue is purified on a 2.6×113 cm column filled with Sephadex G-25 using 10% aqueous acetic acid solution as eluent. The elution is controlled by measuring the UV absorption (287 nm) and thin-layer chromatography. The fractions comprising the desired substance are evaporated, the residue is lyophilized thus 904 mg of crude title product are obtained. This is further purified as described hereinabove on a filling of Sephadex G-25.

The fractions comprising the title peptide are unified, evaporated and the residue is lyophilized. 755 mg of product are obtained which is further purified by middle-pressure liquid chromatography. A reverse phase Whatman LRP-1 filling of a particle size 13 to 24 μm, containing alkyl groups having 1 to 18 carbon atoms and a 2.5×40 cm column used as stationary phase, while a mixture of i-propanol and 0.1% aqueous trifluoracetic acid is used as eluent. The ratio of the organic component is increased to 25% from 2% in the course of the gradient elution. The volume of the eluent used is 400–400 ml. The pure fractions are combined, evaporated and lyophilized. Thus 500 mg (41.6%) of pure, title product are obtained.

Molar weight: 1454

$R_f^6 = 0.60$; $R_f^{10} = 0.60$; $R_f^4 = 0.06$; $R_f^{13} = 0.61$.

EXAMPLE 2

Glp-His-Trp-Ser-Tyr-Asu-Leu-Arg-Pro-ethylamide-dihydrochloride 25 mg (0.071 millimoles) of Glp-His-Trp-Ser-Tyr-Asp(OMe)-Leu-Arg-Pro-ethylamide-bis(trifluoroacetate) prepared according to Example 1 are dissolved in 8 ml of dimethyl formamide, 1.2 ml (8.64 millimoles) of triethyl amine are added and the solution is left to stand for 88 hours at 25° C. Then the reaction mixture is evaporated, just after 30 ml of acetic acid are added and the solvent is evaporated off. The residue is triturated with ether, the ether is decanted and lyophilized. The lyophilized product is dissolved in 5.2 ml of 0.01N aqueous hydrochloric acid solution and the solution is lyophilized again. Thus 21.4 mg (98.7%) of title product are obtained.

Molar weight: 1267.
$[\alpha]_D^{25} = 52.1°$ (c=1.1%, methanol)
$R_f^6 = 0.57$; $R_f^{10} = 0.58$.

EXAMPLE 3

Glp-His-Trp-Ser-Tyr-Asp(OBzl)-Leu-Arg-Pro-ethylamide-diacetate (a) Boc-Asp(OBzl)-Leu-Arg-Pro-ethylamide 490 mg of Leu-Arg-Pro-ethylamide dihydrochloride are dissolved in 10 ml of dimethyl formamide, then the solution is cooled to a temperature of 0° C. and 5 mg Boc-Asp(OBzl)-OPFP in 10 ml of dimethyl formamide are added under stirring. Then the pH of the reaction mixture is adjusted to 7 by the addition of triethyl amine (280 μl), and the stirring is continued for 1 hour at 0° C. and 12 hours at room temperature. The solvent is removed in vacuo, the residue is purified on a 2×95 cm silica gel column using a 90:20:6:11 mixture of ethyl acetate/pyridine/acetic acid/water. The fractions comprising the title product are combined, evaporated in vacuo, the evaporation residue is triturated with ether. Thus 110 mg of title product are obtained in the form of a white powder.

Melting point: 111°–113° C.
$R_f^1 = 0.45$ (b) H-Asp(OBzl)-Leu-Arg-Pro-ethylamide-bis(trifluoroacetate)

210 mg of Boc-Asp(OBzl)-Leu-Arg-Pro-ethylamide in 4 ml of trifluoroacetic acid are stirred for 30 minutes at room temperature. Then the reaction mixture is evaporated in vacuo, the residue is triturated with ether, filtered and dried. Thus 210 mg of solid title compound are obtained.

Melting point: 98°–103° C.
$R_f^1 = 0.25$.

(c) Glp-His-Trp-Ser-Tyr-Asp(OBzl)-Leu-Arg-Pro-ethylamide-diacetate 100.3 mg of Glp-His-Trp-Ser-Tyr-N₂H₃ pentapeptide hydrazide are dissolved in 2 ml of dimethyl formamide, the solution is cooled to −10° C. and 100 μl 6N aqueous hydrochloric acid solution then a concentrated aqueous solution of 11 mg of sodium nitrite are added.

After 5 minutes 116 mg of H-Asp(OBzl)-Leu-Arg-Pro-ethylamide-bis(trifluoracetate) salt in 0.5 ml of dimethyl formamide and 100 μl of triethyl amine are added to the stirred reaction mixture. Then if necessary the pH is adjusted to 7. The stirring is continued at −10° C. for one hour, then at 0° C. for 24 hours. Thereafter the solvent is evaporated in vacuo, the residue is fractionated on a 1×60 cm column filled with Sephadex G-25 filling by using 10% by weight aqueous acetic acid solution as eluent. After combining the appropriate fractions, evaporating the same the residue thus obtained is purified by the reverse phase chromatography described in Example 1. A mixture of 10% by volume of 2-propanol and 90% by volume of 0.1% by weight of aqueous trifluoroacetic acid (350 ml) is used as solvent in a manner that the volume ratio of 2-propanol should reach the 40% at the end of the purification. The fractions comprising the title compound are combined and evaporated, dissolved in a diluted aqueous acetic acid solution and lyophilized. Thus 80 mg of solid title compound are obtained.

$R_f^6 = 0.6$.

Amino acid analysis: Asp=0.99; Ser=0.79; Glu=1.03; Pro=1.0; Leu=1.3; Tyr=0.83; His=0.77; Arg=1.2.

Tryptophan and ethylamine have not been determined.

EXAMPLE 4

Glp-His-Trp-Ser-Dbt-Asp(OMe)-Leu-Arg-Pro-ethylamide-diacetate (a) Boc-Trp-Ser-Dbt-OMe 42 g of Boc-Trp-OPFP amino acid derivative and 4.6 g of H-Ser-Dbt-OMe dipeptide are dissolved in a mixture of 60 ml of dioxane and 20 ml of ethyl acetate cooled to 0° C., then the solution is stirred for an hour at 0° C. and for 24 hours at 20° C. Then the solvent is distilled off from the reaction mixture, the residue is dissolved in ethyl acetate and extracted three-three times with 5% by weight of aqueous citric acid solution at 0° C., then saturated aqueous sodium hydrogencarbonate solution, then with saturated aqueous sodium chloride solution. The organic phase is dried over anhydrous sodium sulfate, filtered and evaporated in vacuum. The residue is dissolved in ethyl acetate and precipitated by adding petrolether. The precipitated substance is filtered, washed with petrolether and dried. Thus 6.0 g of title product are obtained.

Molar weight: 727.
$R_f^5 = 0.75$. Mp: 118°–121° C.

(b) H-Trp-Ser-Dbt-OMe hydrochloride 3.5 g of Boc-Trp-Ser-Dbt-OMe tripeptide are dissolved in 60 ml of 4N methanolic hydrogen chloride solution, then the solution is stirred for 2 hours at 20° C. The solvent is evaporated in vacuo, the residue is dissolved in methanol, and evaporated again in vacuo. The evaporation residue is dried over solid sodium hydroxide in vacuo, and precipitated from ethanol by the addition of ether, filtered and dried. Thus 2.5 g of title product are obtained.

Molar weight: 663.
Melting point: 215°–217 ° C.
$R_f^1 = 0.45$.

(c) Glp-His-Trp-Ser-Dbt-OMe 393 mg of Glp-His-N₂H₃ dipeptide hydrazide are suspended in 3.5 ml of dimethyl formamide, 0.7 ml of 6N aqueous hydrochloride solution are added and the suspension is cooled to −10° C. Then 106 mg of sodium nitrite in the form of a concentrated aqueous solution are added then after 5 minutes 927 mg of H-Trp-Ser-Dbt-OMe hydrochloride in 3.5 ml of dimethyl formamide and 0.1 ml of triethyl amine cooled to −5° C. are introduced. Thereafter the pH of the solution is adjusted to 7 if necessary by triethyl amine, then the reaction mixture is stirred at −5° C. for 1 hour, then at 0° C. for 2 hours. The solvent is evaporated in vacuo, the residue is triturated with ethyl acetate then ether and filtered off. The crude product thus obtained is chromatographed on a silica gel column (98×2 cm) using eluent mixture No. 4 as solvent. The fractions comprising the desired substance are combined, evaporated and the residue is triturated with ether. Thus 850 mg of title product are obtained.

Molar weight: 875.

$R_f^1 = 0.3$.

Amino acid analysis: Ser=0.90; Glu=1.05; His=0.99; Trp=1.00.

Dbt has not been determined.

(d) Glp-His-Trp-Ser-Dbt-N$_2$H$_3$ 280 mg of Glp-His-Trp-Ser-Dbt-OMe pentapeptide are dissolved in 5 ml of dimethyl formamide, 0.8 ml of hydrazine hydrate are added, and the solution is stirred for 24 hours at 60° C. The precipitated substance is filtered off, washed with water then dissolved in solvent mixture No. 11 and chromatographed on a 98×2 cm column filled with Sephadex G-25 filling. The fractions comprising the main component are combined, evaporated, the evaporation residue is triturated with ether and dried. Thus 205 mg (70%) of title product are obtained. Molar weight: 875.

$R_f^1 = 0.25$.

(e) Glp-His-Trp-Ser-Dbt-Asp(OMe)-Leu-Arg-Pro-ethylamide diacetate 45 mg of Glp-His-Trp-Ser-Dbt-N$_2$H$_3$ pentapeptide hydrazide are dissolved in 1 ml of dimethyl formamide, the solution is cooled to −20° C., then 0.035 ml of 6N aqueous hydrochloric acid solution and 3.8 mg of sodium nitrite in the form of a concentrated aqueous solution are added under stirring. After 15 minutes 31 mg of H-Asp(OMe)-Leu-Arg-Pro-ethylamide diacetate in 0.5 ml dimethyl formamide, after another 5 minutes 0.3 ml of 10% triethyl amine dissolved in dimethyl formamide are added to the reaction mixture at −10° C. under stirring. The stirring is maintained for 30 minutes at −10° C., for 1 hour at 0° C., finally for 48 hours at 24° C.

Then the dimethyl formamide is evaporated in vacuo, the residue is dissolved in 10% by weight of aqueous acetic acid solution and chromatographed on a 60×2 cm column filled with Sephadex G-25 filling. The fractions comprising the main components are combined and imophilized. Thus 35 mg of title product are obtained.

Molar weight: 1502.

$R_f^6 = 0.2$.

EXAMPLE 5

Glp-His-Trp-Ser-Tyr-Asu-Leu-Arg-Pro-ethylamide diacetate 50 mg of

Glp—His—Trp—Ser—Tyr—Asp—OMe  Leu—Arg— diacetate are dissolved in 15 ml of dimethyl formamide and 2.4 ml of triethyl amine are added and the solution is stirred at room temperature for 50 hours. Then the reaction mixture is evaporated in vacuo, the residue is dissolved in 30 ml of acetic acid and evaporated again. The residual oily substance is triturated with other, filtered, dried and dissolved in dilute acetic acid and lyophilized. Thus 48.2 mg (98%) of title product are obtained.

$[\alpha]_D^{25} = -50.3°$ (c=1.0; 1% acetic acid solution)

$R_f^6 = 0.57$; $R_f^7 = 0.58$.

EXAMPLE 6

Glp-His-Trp-Ser-Tyr-Asu-Leu-Arg-Pro-ethylamide-bis(trifluoroacetate)

(a) Z-Asu-Leu-Arg(NO$_2$)-pro-ethylamide 300 mg of Z-Asp(OMe)- Leu-Arg(NO$_2$)-Pro-ethylamide tetrapeptide prepared according to Example 1/a are dissolved in 100 ml of dimethyl formamide, 5.7 ml of triethyl amine are added and the mixture is stirred at room temperature for 60 hours. Then the reaction mixture is evaporated in vacuo, the residue is dissolved in acetic acid and evaporated again. The oily residue thus obtained is triturated with ether, filtered and dried. Thus 282 mg (98%) of title product are obtained.

Molar weight: 687.

Melting point: 112°–115° C.

$R_f^9 = 0.34$; $R_f^2 = 0.84$.

(b) H-Asu-Leu-Arg-Pro-ethylamide diacetate 280 mg of Z-Asu-Leu-Arg(NO$_2$)-Pro-ethylamide are dissolved in a mixture of 3 ml of methanol and 3 ml of acetic acid and in the presence of 140 mg of 10% palladium on charcoal, hydrogen gas is bubbled through the mixture for 7 hours. Then the catalyst is filtered off, the filtrate is evaporated in vacuo, the residue is triturated with ether, filtered and dried. Thus 226 mg (88%) of solid, slightly hygroscopic title product are obtained.

Molar weight: 628.

$[\alpha]_D^{25} = -45.2°$ (c=1.0, methanol)

$R_f^4 = 0.29$; $R_f^6 = 0.60$; $R_f^{13} = 0.50$.

(c) Glp-His-Trp-Ser-Tyr-Asu-Leu-Arg-Pro-ethylamide-bis(trifluoroacetate)

The method described in Example 1/c is followed except that 217 mg of Glp-His-Trp-Ser-Tyr-N$_2$H$_3$ pentapeptide hydrazide and 171 mg of H-Asu-Leu-Arg-Pro--ethylamide diacetate are used as starting materials.

EXAMPLE 7

Glp-His-Trp-Ser-Tyr(3,5-$^3$H)-Asp(OMe)-Leu-Arg-Pro-ethylamide 2 mg of Glp-His-Trp-Ser-Dbt-Asp(OMe)-Leu-Arg-Pro-ethylamide diacetate are dissolved in 0.5 ml of 1N acetic acid solution and the solution is frozen. To the upper part of the frozen solution 10 mg of 10% palladium-aluminium oxide catalyst (produced by Fluka) are poured, then tritium gas is introduced. Then the reaction mixture is heated to 0° C. and tritiated for 30 minutes under stirring. The excess of tritium gas is led away, the reaction mixture is diluted with 10 ml of 0.1N acetic acid solution, filtered, finally the solvent is removed in vacuo. The product is purified on an analytical high-pressure chromatographic column (filling: Shandon ODS-Hypersyl of 5 μm particle size; coloumn 25×0.5 cm) using 43% by volume of methanol and 57% by volume of 0.1M ammonium acetate/acetic acid buffer of a pH of 4.0 as eluent. Thus a labelled product of a specific radioactivity of 1-2 Ci/mM is obtained, which ph/sical and chemical characteristics are the same as that of the non-radioactive product (product of Example 1/c).

EXAMPLE 8

Formulation example 10 mg of Asu$^6$, desGly$^{10}$-GnRH-ethylamide dihydrochloride are dissolved in 0.1 ml of benzylalcohol suitable for the preparation of injection formulations. The benzyl alcoholic solution thus obtained is diluted to 100 ml with (a) distilled water suitable for the preparation of aqueous injections, or (b) an oil suitable for the preparation of oily injections.

The solution thus obtained is filtered to sterile and filled into sterile ampoules in a manner known per se

What is claimed is:

1. A compound of the Formula (I)

Glp-His-Trp-Ser-X-Asu-Leu-Arg-Pro-Y wherein

X is Phe, Tyr, Tyr (3,5-$^3$H) or 3,5-dibromo-tyrosyl; and

Y is glycinamide, aza-glycinamide, or alkylamino having 1 to 4 carbon atoms, or a pharmaceutically acceptable acid addition salt thereof.

2. The compound of the Formula (I) defined in claim 1 wherein X is Tyr and Y is alkylamino having 1 to 4 carbon atoms, or a pharmaceutically acceptable acid addition slat thereof.

3. Glp-His-Trp-Ser-Tyr-Asu-Leu-Arg-Pro-ethylamide or a pharmaceutically acceptable acid-addition salt thereof as defined in claim 2.

* * * * *